United States Patent [19]

Cai et al.

[11] Patent Number: 5,613,945
[45] Date of Patent: Mar. 25, 1997

[54] PORTAL ASSEMBLY

[75] Inventors: Qingsheng Cai, St. Paul; William L. Beling, New Brighton; Jerald Glantz, Lake Elmo; Theodore A. Johnson, St. Paul, all of Minn.

[73] Assignee: SIMS Deltec, Inc., St. Paul, Minn.

[21] Appl. No.: 475,979

[22] Filed: Jun. 7, 1995

Related U.S. Application Data

[63] Continuation of Ser. No. 184,655, Jan. 21, 1994.
[51] Int. Cl.$^6$ .................................................. A61M 11/00
[52] U.S. Cl. ............................. 604/93; 604/116; 604/175
[58] Field of Search ............................. 604/8, 9, 86, 93, 604/175, 905, 116, 80, 43, 280, 131, 132, 133, 140, 256, 244, 218, 201, 283, 200

[56] References Cited

U.S. PATENT DOCUMENTS

| | | |
|---|---|---|
| 1,042,098 | 10/1912 | English . |
| 1,481,341 | 1/1924 | Bersted . |
| 2,907,591 | 10/1959 | Gulick . |
| 3,262,718 | 7/1966 | Draudt . |
| 3,441,296 | 4/1969 | Wilkin . |
| 3,585,654 | 6/1971 | Jacobs . |
| 4,033,613 | 7/1977 | Bram . |
| 4,273,272 | 6/1981 | Blanc . |

(List continued on next page.)

FOREIGN PATENT DOCUMENTS

| | | |
|---|---|---|
| 528494 | 3/1957 | Belgium . |
| 782512 | 6/1935 | France . |
| 2628639 | 9/1989 | France . |
| 4129781 | 3/1993 | Germany . |

OTHER PUBLICATIONS

Exhibit 1: "DAVOL Implanted Ports with Groshong™ Catheter—Use and Maintenance", Bard Access Systems, Salt Lake City, UT; Feb. 1992. (11 pages).

Exhibit 2: "Implanted Ports with Hickman® Catheter—Use and Maintenance", Bard Access Systems, Salt Lake City, UT; Feb. 1992. (14 pages).

Exhibit 3: Photograph: CELSA product. (1 page).

Exhibit 4: "Chemo–Port® Implantable Vascular Access Ports", HDC Corporation, San Jose, CA; 1991. (4 pages).

Exhibit 5: "TrimPort™ Series Superior Vascular Access", Gerard Medical, Inc., Massachusetts; undated. (3 pages).

Exhibit 6: "For secure fluid delivery to vascular access ports," Gish Biomedical, Inc., Irvine, CA; Mar.–Apr. 1993. (3 pages).

OTHER PUBLICATIONS

Exhibit M—"Oncology/Critical Care", Quinton Instrument Company (an A.H. Robins Company), Seattle, WA, 4 pages, dated Jul. 1988.

Primary Examiner—Corrine M. McDermott
Assistant Examiner—N. Kent Gring
Attorney, Agent, or Firm—Merchant, Gould, Smith, Edell, Welter & Schmidt P.A.

[57] ABSTRACT

A portal assembly includes a port with at least one resealable septum, and a tube extending from the port with the tube being sized to be received inside a catheter, an angled surface surrounding the tube wherein the angled surface diverges away from the tube in a direction away from the port, and sleeve structure for forcing the end of the catheter into the angled surface, thereby forcing the end of the catheter radially inwardly toward the tube and forming a thickened portion adjacent the end of the catheter to seal and hold the catheter. In a dual port construction, the outlet tube are parallel to one another at their distal ends, and the sleeve structure forces the end of the catheter into the angled surface, thereby forcing the end of the catheter radially inwardly toward the tubes and forming a thickened portion adjacent the end of the catheter to seal and hold the catheter and to prevent cross-talk between lumens of a dual lumen catheter.

11 Claims, 5 Drawing Sheets

U.S. PATENT DOCUMENTS

| | | |
|---|---|---|
| 4,296,949 | 10/1981 | Muetterties et al. . |
| 4,325,571 | 4/1982 | Funderburg et al. . |
| 4,452,473 | 6/1984 | Ruschke . |
| 4,592,749 | 6/1986 | Ebling et al. . |
| 4,625,998 | 12/1986 | Draudt et al. . |
| 4,673,394 | 6/1987 | Fenton, Jr. . |
| 4,675,007 | 6/1987 | Terry . |
| 4,692,146 | 9/1987 | Hilger . |
| 4,704,103 | 11/1987 | Stober et al. . |
| 4,723,948 | 2/1988 | Clark et al. . |
| 4,735,442 | 4/1988 | Burli . |
| 4,772,270 | 9/1988 | Wiita et al. . |
| 4,772,276 | 9/1988 | Wiita et al. . |
| 4,781,680 | 11/1988 | Redmond et al. . |
| 4,810,241 | 3/1989 | Rogers . |
| 4,834,719 | 5/1989 | Arenas . |
| 4,838,873 | 6/1989 | Landskron et al. . |
| 4,861,341 | 8/1989 | Woodburn . |
| 4,880,414 | 11/1989 | Whipple . |
| 4,915,690 | 4/1990 | Cone et al. . |
| 4,929,236 | 5/1990 | Sampson . |
| 4,929,243 | 5/1990 | Koch et al. . |
| 4,963,133 | 10/1990 | Whipple . |
| 4,969,879 | 11/1990 | Lichte . |
| 4,994,048 | 2/1991 | Metzger . |
| 5,026,344 | 6/1991 | Dijkstra et al. . |
| 5,041,098 | 8/1991 | Loiterman et al. . |
| 5,045,060 | 9/1991 | Melsky et al. . |
| 5,084,015 | 1/1992 | Moriuchi ................................. 604/93 |
| 5,108,377 | 4/1992 | Cone et al. . |
| 5,129,891 | 7/1992 | Young . |
| 5,147,483 | 9/1992 | Melsky et al. . |
| 5,149,330 | 9/1992 | Brightbill . |
| 5,167,638 | 12/1992 | Felix et al. . |
| 5,178,612 | 1/1993 | Fenton, Jr. . |
| 5,180,365 | 1/1993 | Ensminger et al. . |
| 5,185,003 | 2/1993 | Brethauer . |
| 5,213,574 | 5/1993 | Tucker . |
| 5,312,337 | 5/1994 | Flaherty et al. . |
| 5,360,407 | 11/1994 | Leonard . |
| 5,387,192 | 2/1995 | Glantz et al. . |
| 5,395,324 | 3/1995 | Hinrichs et al. .................... 604/93 |
| 5,399,168 | 3/1995 | Wadsworth et al. . |

OTHER PUBLICATIONS

Exhibit 7: "A–Port™ Implantable Vascular Access System", Therex Corporation, Walpole, MA; 1992. (2 pages).

Exhibit 8: "Vascular Access Products", Strato Medical Corporation/Pfizer, Beverly, MA; Sep. 1991. (8 pages).

Exhibit A—"S.E.A.—Port™ Side Entry Access Port" by Harbor Medical Devices, Inc., 6 pages, dated 1988.

Exhibit B—"Turning Vascular Access on its Side—S.E.A.–Port™ Implantable Access Systems", Harbor Medical Devices, Inc., 2 pages, dated 1989.

Exhibit C—"Access Ability—the S.E.A.–Port® Topsider™", Harbor Medical Devices, Inc., Jaffrey, NH, 4 pages, dated 1991.

Exhibit D—"Thurning Vascular Access on its Side—S.E.A.–Port™", Harbor Medical Devices, Inc., Jaffrey, NH, 5 pages, undated.

Exhibit E—"Covering the Angeles on Access", Harbor Medical Devices, Inc., Jaffrey, NH, 4 pages, dated 1989.

Exhibit F—"Norport™–LS Vascular–Access Port", Norfold Medical, Skokie, IL, 1 page, undated.

Exhibit G—"Omegaport™ Implantable Access System for All Therapies", Norfolk Medical, Skokie, IL, 1 page, dated Jan. 1, 1992.

Exhibit H—"Sure Cath® Port Access Catheter", Ivion Corporation, Broomfield, CO, 2 pages, dated 1992.

Exhibit I—"The Key to a Good Vascular Access Port System is Using the Right Combination.", Gish Biomedical, Inc., Irvine, CA, 4 pages, dated 1987.

Exhibit J—"ImPort™—Vascular Access Port", Pudenz-Schulte Medical Corporation, Goleta, CA, 2 pages, undated.

Exhibit K—"Functionally Superior", Therex Corporation, Walpole, MA, 2 pages, dated 1992.

Exhibit L—"Dimensionally Distinctive", Therex Corporation, Walpole, MA, 2 pages, undated.

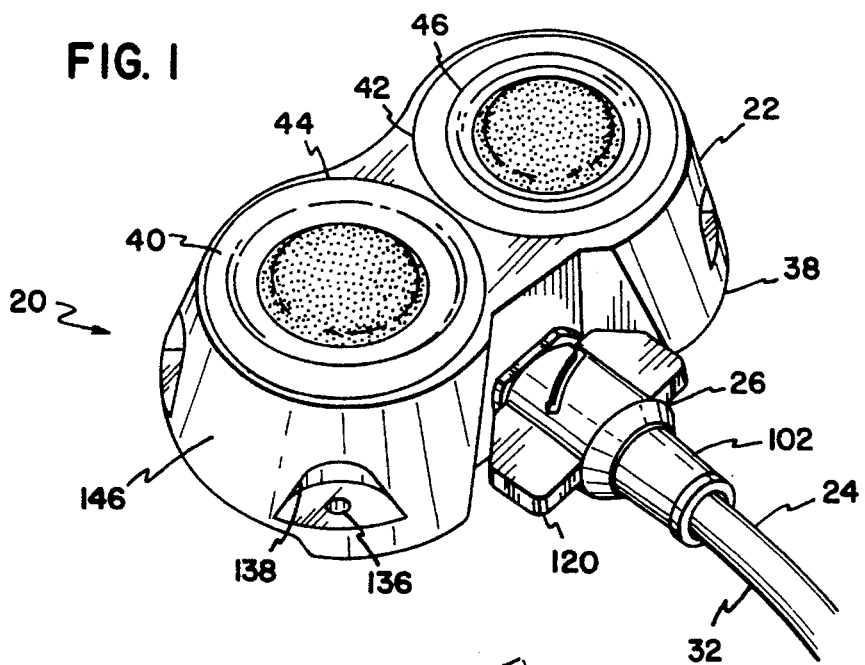
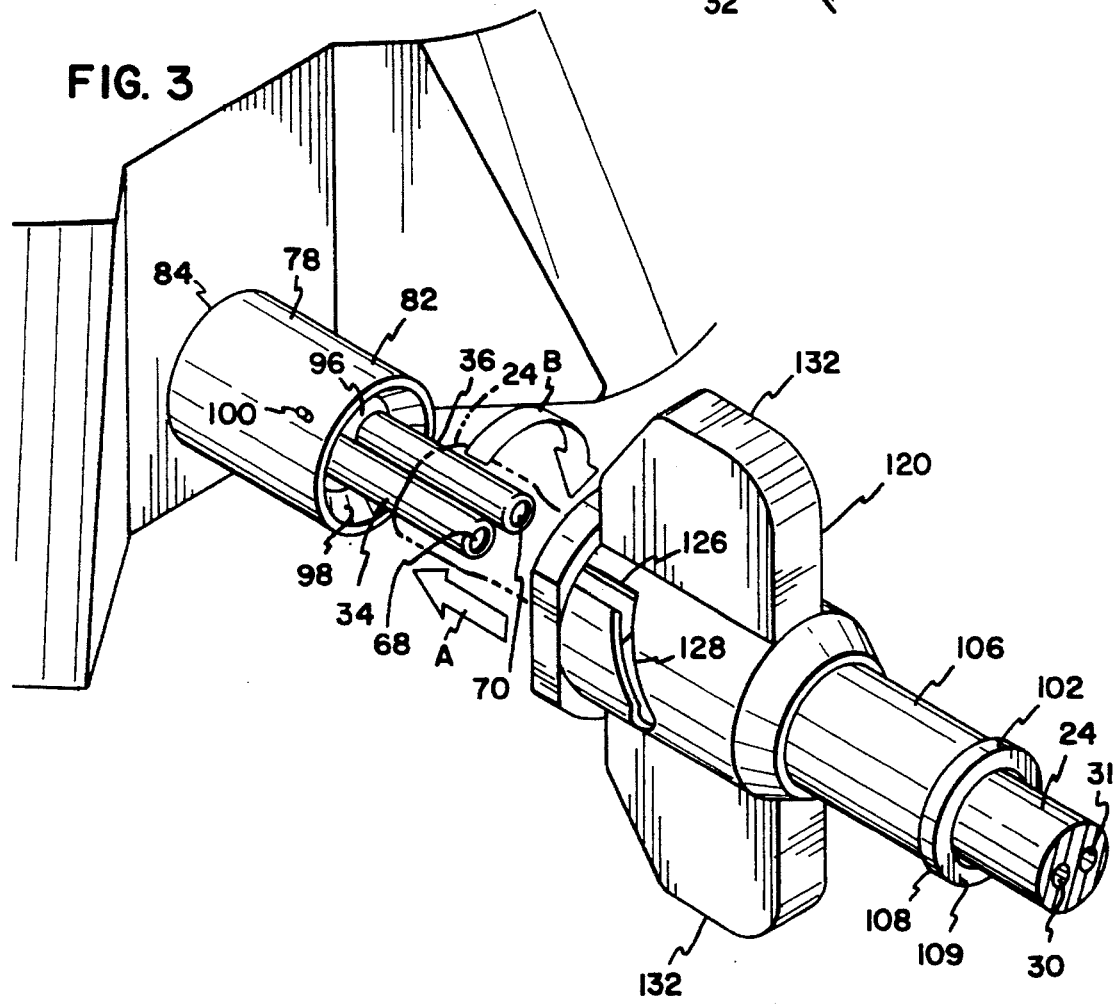

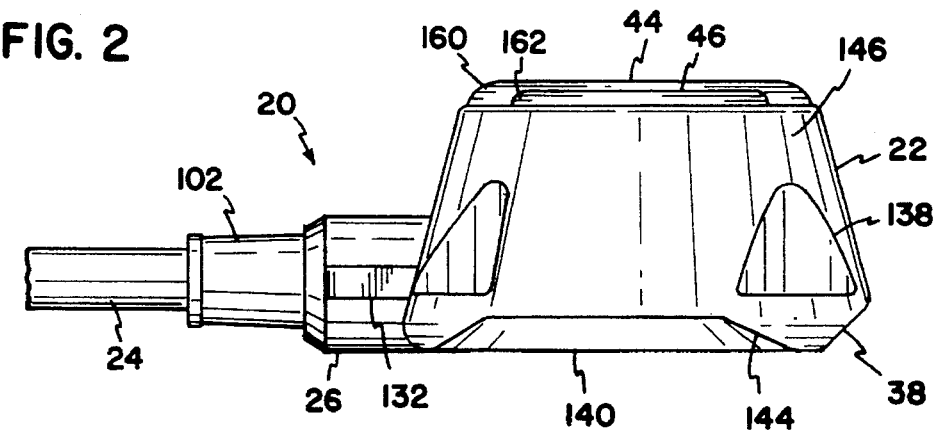
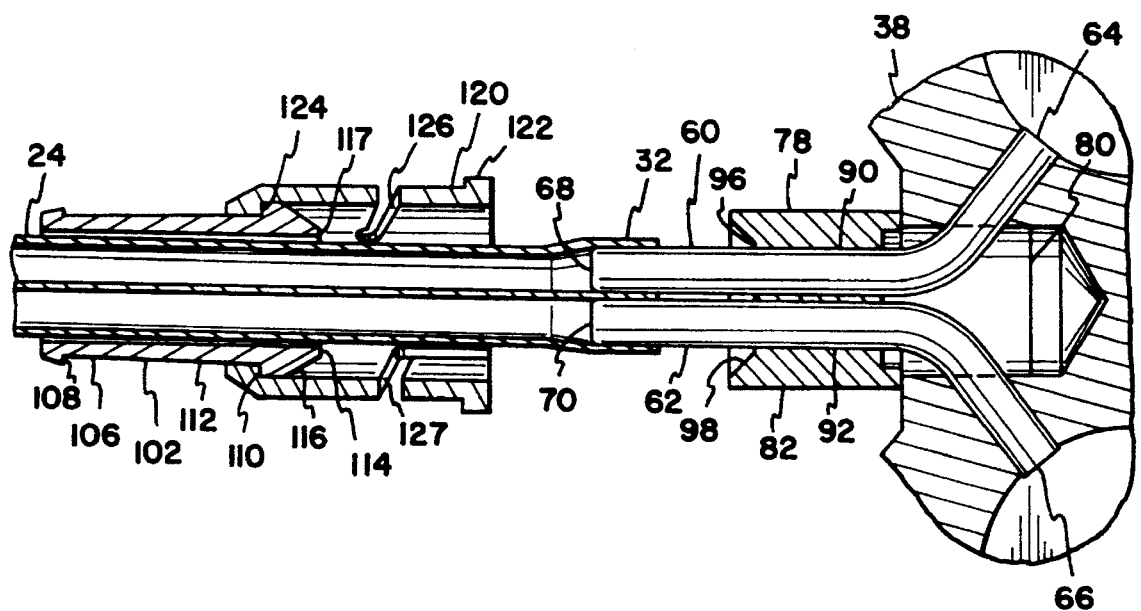

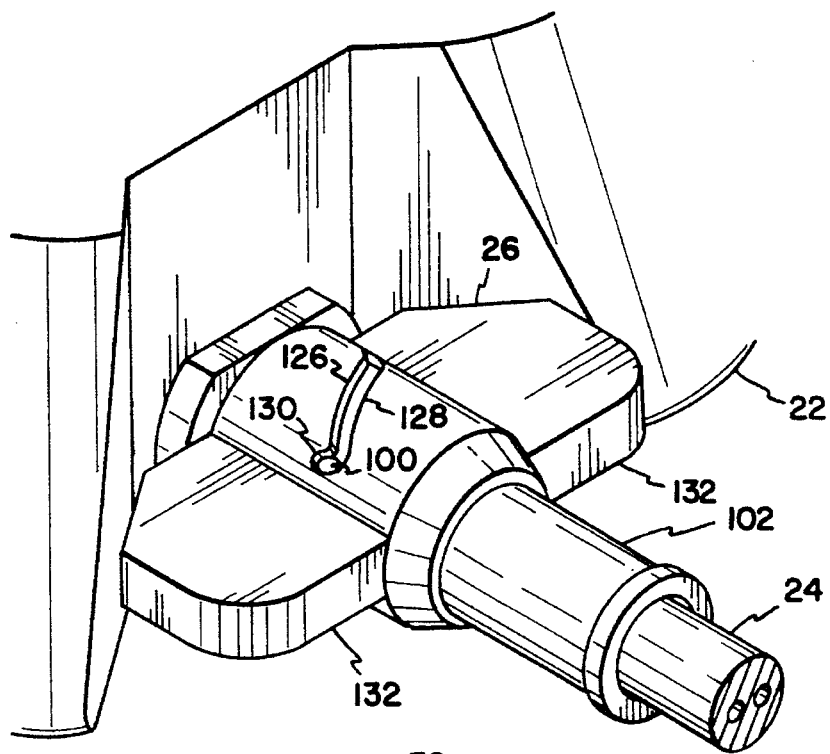
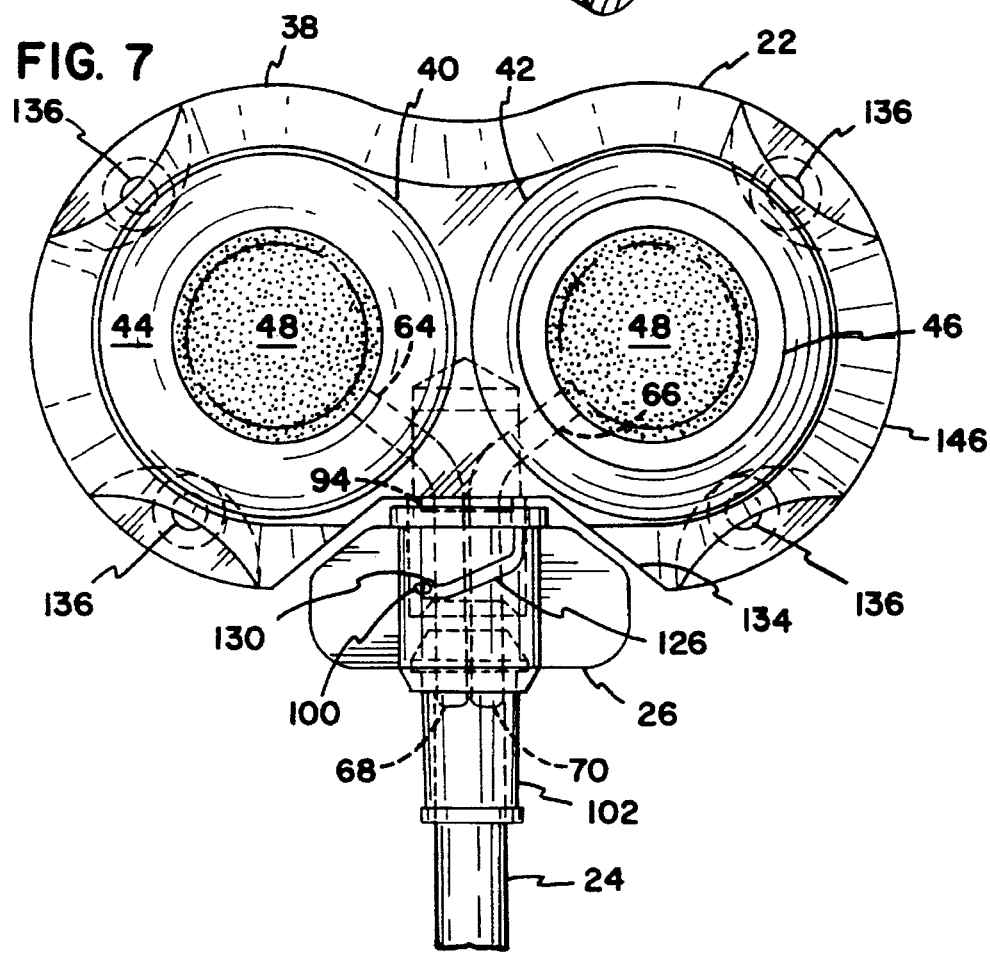

PORTAL ASSEMBLY

This is a Continuation of application Ser. No. 08/184,655, filed Jan. 21, 1994, which application is incorporated herein by reference.

FIELD OF THE INVENTION

This invention relates to catheter connectors and methods for connection generally, and more specifically to catheter connectors and methods for portal assemblies.

BACKGROUND OF THE INVENTION

The treatment of certain diseases of the human body or an animal's body often requires infusion of drugs, blood products, nutritional fluids, or other fluids into the patient's venous or arterial system, the patient's peritoneal or epidural space, or other locations within the patient's body. One system which is useful when repeated access for infusion is needed utilizes an implanted portal assembly which is accessed percutaneously to infuse the fluid to the desired location. A similar arrangement can be used to draw blood from an artery or vein for blood sampling purposes, or to draw other body fluids.

Such an implanted assembly includes a port which is implanted under the skin and attached to the chest wall or other convenient body location. The port includes a septum for accessing an interior of the port. The septum is located directly under the skin and is penetrable by a needle. Drugs or other fluids can be introduced into the port (or fluids withdrawn from the port) by percutaneously inserting the needle through the septum of the port. The port includes an outlet member which is connected via connection structure to one end of a flexible elastic catheter which leads to the infusion (or withdrawal) site in the patient's body.

U.S. Pat. No. 4,880,414, issued Nov. 14, 1989, and U.S. Pat. No. 4,723,948, issued Feb. 9, 1988 are two examples of different connection structure for connecting a catheter to a port.

Such an implantable port device of this type may remain in the patient's body for a long period of time, such as several months. A significant concern is that the connection between the catheter and the port remain secure and fluid tight during the period of implantation. The catheter and port may be subjected to various external forces acting to separate the catheter from the port. Should the connection fail, the fluids injected into the port would not be transported to the targeted infusion site and instead the fluid would be dispensed at the site of the port. This can be a particular concern in the case of certain drug therapies, such as chemotherapy, in which the drugs are highly concentrated and dangerous if misdirected in the patient's body. Withdrawal of fluids would also be adversely affected if the connection failed.

A further concern is the ease and reliability in which the port can be connected to the catheter. Typically, the connection between the port and the catheter is made during the implantation surgery when the portal assembly is first installed. A surgeon handling the implantation surgery will be wearing gloves, and the gloves or port may be covered with body fluids from the surgery. There is a need for the connector structure to be easy to use in these circumstances and to do so reliably. There is also a need for the connection to be made quickly to keep the length of the surgery as short as possible.

Another concern with respect to implantable devices of this type is that it may be necessary to disconnect the catheter from the port after implantation if the catheter or port needs to be changed. One concern is whether the connection between the catheter and port is easily disconnectable.

A further concern is the size of the catheter connector. A-connector that is too bulky can be a problem for the patient. Intricate parts can be a problem for manufacture of the connector, and also use of the connector, especially if the parts are small in size.

There has been a long felt need in the art for catheter connectors and connection methods generally, and more specifically catheter connectors and methods for connecting catheters to ports which address at least some of the above concerns and other concerns in the art.

SUMMARY OF THE INVENTION

One aspect of the invention relates to a portal assembly for connecting to a catheter wherein the assembly includes a port with a resealable septum. A tube extends from the port wherein the tube is sized to be received inside the catheter. An angled surface surrounds the tube. The angled surface diverges away from the tube in a direction away from the port. A sleeve structure draws the catheter toward the angled surface wherein the catheter bunches up and is wedged generally radially inwardly toward the tube. The catheter is forced into the angled surface thereby forcing the end of the catheter against the tube to seal the catheter, and also forming a thickened portion of the catheter to hold the catheter to the port.

In one preferred embodiment, a dual port is provided wherein the dual port includes two septums and two separate internal chambers. An outlet tube extends from each internal chamber. The outlet tubes extend from the port in a parallel direction at their distal ends. In the dual port arrangement, the catheter is a dual lumen catheter and the angled surface surrounds both tubes wherein the angled surface defines a generally truncated conical shape with the two tubes centered around the longitudinal axis of the truncated conical shape. Preferably, different sized rings are provided including different heights, and preferably different widths, for palpitation by the caregiver to distinguish the two septums.

The sleeve structure in the preferred embodiment includes a sleeve with a tip formed by an angled surface, preferably conically shaped, which diverges away from the port. The angled tip is located adjacent the thickened portion of the catheter, and assists in keeping the catheter from being pulled out by anchoring the thickened portion. A lock ring in the preferred embodiment is rotatably mounted to the sleeve. Twist lock structure moves the lock ring and sleeve toward the port and holds the lock ring and sleeve in the locked position to thereby seal and hold the catheter to the tube.

A further aspect of the invention relates to a connector for a catheter including: a base arrangement having a tube extending from the base arrangement and terminating at an end, with the tube being sized to be received inside the catheter; and a concavely shaped surface surrounding the tube, with the concavely shaped surface diverging away from the tube in a direction away from the base arrangement, and the concavely shaped surface sized to engage an end of the catheter. A sleeve arrangement is engageable with the catheter, with the sleeve arrangement having an inside diameter smaller than an outside diameter of the end of the catheter when the end of the catheter is positioned on the end of the tube. Structure is provided for mounting the sleeve arrangement to the base arrangement. The sleeve arrangement preferably includes a convexly shaped tip diverging away from the base arrangement. The base arrangement further preferably includes a second tube extending from the port generally parallel to the first tube, and the angled surface also surrounds the second tube.

A further aspect of the invention relates to a connector for a catheter wherein a sleeve arrangement, preferably including a lock ring and a sleeve, cooperates to mount a catheter to a tube of a base arrangement. Preferably, the lock ring mounts to the base arrangement and is further rotatably mounted to the sleeve. Preferably, the sleeve arrangement includes a cam slot for receiving a bayonet of the base arrangement, and an overcenter portion in the cam slot holds the sleeve arrangement in a locked position.

A further aspect of the invention relates to a dual port construction including two angled outlet tubes which include distal ends extending generally parallel to one another. A further aspect of the invention relates to a method of assembly including insertion of a proximal end of a first angled outlet tube into a port, insertion of proximal end of a second angled outlet tube into the port, then rotation of the first angled outlet tube until distal ends of each outlet tube are parallel.

Another aspect of the invention relates to a method of using a portal assembly including the steps of: providing a port with a tube extending therefrom, positioning an end of a catheter on the tube, and forming the end of the catheter into a thickened wedge shape. In one preferred form of the method, two parallel tubes are provided, and the catheter is a dual lumen.

A further aspect of the invention relates to a method of using a portal assembly including the steps of: providing a port with a tube extending therefrom, the port including an angled surface surrounding the tube, and the angled surface diverging away from the tube in a direction away from the port. The method further includes positioning an end of a catheter on the tube, and forcing the catheter into the angled surface to force the end of the catheter generally radially inwardly against the tube and to form a thickened portion adjacent the end of the catheter. In one preferred form of the method, two parallel tubes are provided, and the catheter is a dual lumen.

Another aspect of the invention relates to a portal assembly including a housing construction defining an internal chamber, and a septum mounted to the housing construction to permit access to the internal chamber, wherein the housing construction defines a plurality of suture holes. Each suture hole has a first passage, and a lead-in sized larger than the first passage and tapering to the first passage. A depression is preferably formed adjacent each suture hole opposite to the lead-in.

Another aspect of the invention relates to a portal assembly including a housing construction defining an internal chamber, and a septum mounted to the housing construction to permit access to the internal chamber, where the internal chamber includes a bottom surface facing opposite to the septum wherein the bottom surface is defined by a complex curve including a first larger radius defining a central portion and a second smaller radius defining a periphery around the central portion.

BRIEF DESCRIPTION OF THE DRAWINGS

In the drawings, where like numerals refer to like features throughout the several views:

FIG. 1 is a perspective view of a portal assembly according to the present invention including a catheter connector.

FIG. 2 is a side view of the portal assembly shown in FIG. 1.

FIG. 3 is a portion of the portal assembly of FIG. 1, shown prior to full connection of the catheter to the port.

FIG. 4 shows the portion of the portal assembly shown in FIG. 3 once the catheter is fully connected.

FIG. 5 is a portion of the portal assembly shown in FIG. 1 in partial cross-section in a top view and showing the portal assembly prior to full connection of the catheter to the port.

FIG. 7 is a top view of the port assembly shown in FIGS. 1 and 2 with portions of the interior structure shown in dashed lines.

DETAILED DESCRIPTION OF THE PREFERRED EMBODIMENTS

Figure 6:
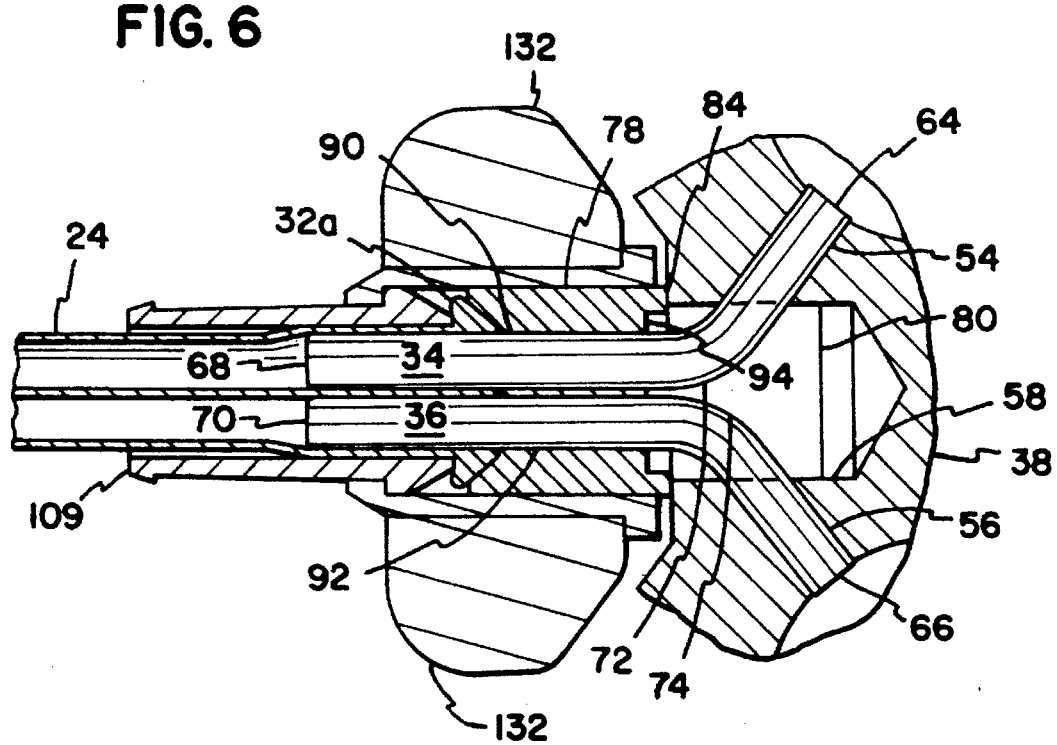
FIG. 6 shows the portion of the portal assembly shown in FIG. 5 once the catheter is fully connected.

The present invention provides a connector for connecting a catheter to a base arrangement. The base arrangement preferably includes an access port for implantation under the skin. The connector forces the end of the catheter into a wedge shape for sealing engagement with an outlet tube of the port. A rotatably mounted sleeve and lock ring of a sleeve arrangement permits the sleeve to remain engaged with the catheter during rotational movement of the lock ring to seal the catheter. A cam/bayonet arrangement with an overcenter portion provides consistent sealing of the catheter, as well as a mechanical advantage for the operator, and secure locking. A preferred configuration of the port is a dual port with parallel outlet tubes engaged with a dual lumen catheter held in place by the connector.

Referring now to FIGS. 1 and 2, a portal assembly 20 is shown. FIGS. 3-12 show features of portal assembly 22 in greater detail. Portal assembly 20 includes a portal or port 22, a catheter 24, and a connector 26 connecting catheter 24 to port 22 with a fluid tight seal. Portal assembly 20 is implantable under the skin for use in infusing drugs or other fluids to the patient entering at port 22 and exiting at a distal end (not shown) of catheter 24. Portal assembly 20 is also utilized in some situations as a port for withdrawing blood or other fluids from the body via catheter 24. In either case, catheter 24 has the distal end at the desired location within the patient's body. Connector 26 connects a proximate end 32 of catheter 24 to port 22. Connector 26 also permits disconnection of catheter 24 from port 22 at the desired time. Catheter 24 is made from a biocompatible and flexible, elastic polymeric material such as silicone.

Figure 10:
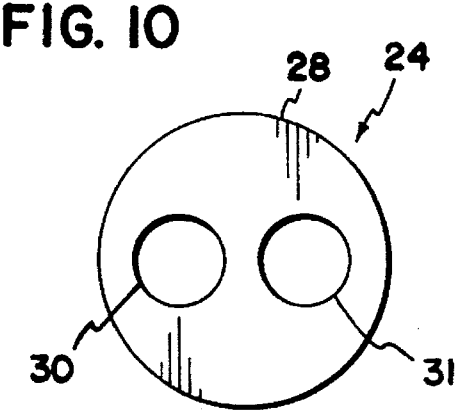
FIG. 10 is an enlarged end view of the dual lumen catheter.
Figure 11:
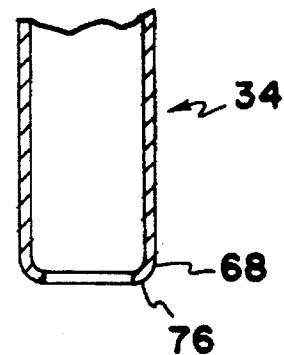
FIG. 11 is an enlarged cross-sectional view of a distal end of one of the outlet tubes extending from the port.
Figure 12:
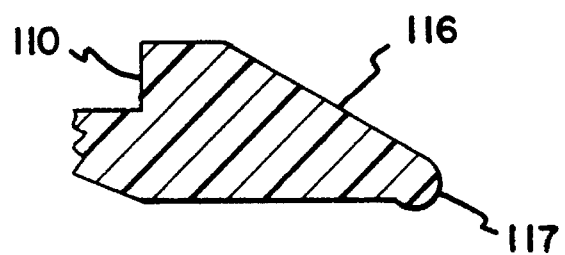
FIG. 12 is an enlarged cross-sectional view of an end of the sleeve.

In the embodiment shown, port 22 is a dual port. Two different needle access sites are provided with a dual port configuration. As will be described below, the dual port configuration includes two outlet tubes 34, 36 as shown in FIG. 3, for example, and catheter 24 is a dual lumen configuration with a first lumen 30 and a second lumen 31 as shown in FIGS. 3 and 10. Distal ends 68, 70 of outlet tubes 34, 36 extend parallel and in close proximity to one another. Each lumen 30 31 is in fluid communication with one of outlet tubes 34, 36. Additional outlet tubes and an appropriately configured catheter 24 can be provided if more than two access sites are provided.

It is to be appreciated that portal assembly 20 can instead be a single port configuration, with a single outlet tube, and catheter 24 be a single lumen. It is also to be appreciated that, for a multi-port configuration, outlet tubes 34, 36 can be positioned in a spaced apart configuration (not shown). In that case, a connector 26 would be provided for each outlet tube and catheter 24 would be a single lumen.

Outlet tubes 34, 36 are shown as being made from tubular shaped biocompatible metallic materials, such as titanium. Other materials, such as plastics and other non-metallic materials, and other shapes, such as a bulbous stem shape, are possible.

Figure 8:
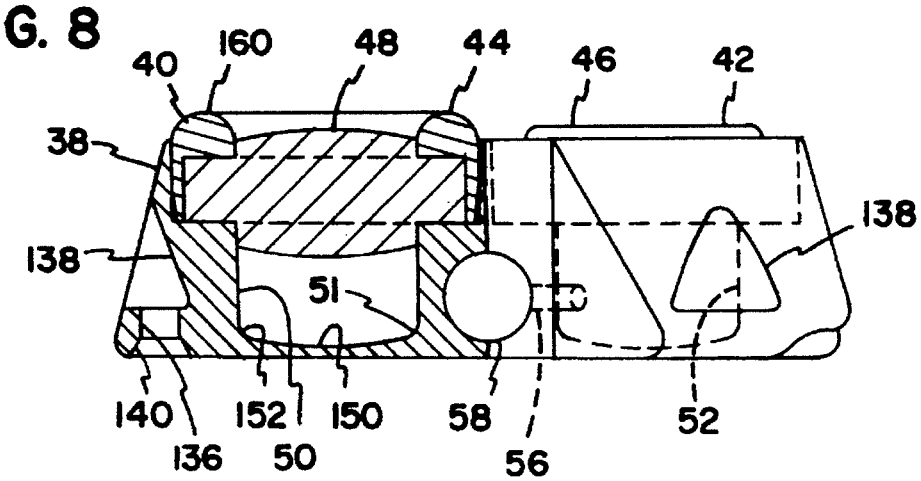
FIG. 8 is a partial cross-sectional side view of the port without the outlet tubes and the insert.
Figure 9:
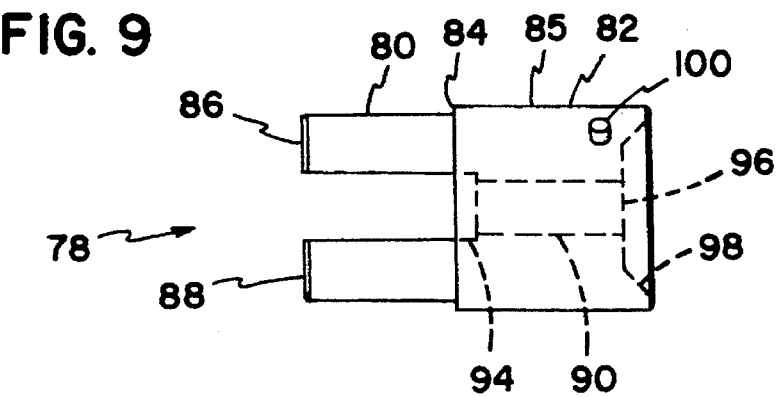
FIG. 9 is an enlarged side view of the insert.

As best shown in FIGS. 7 and 8, port 22 includes a housing or base 38 integrally formed to have two main openings or internal recesses each closed off by a cap 40, 42 which each retains a septum 48. Caps 40, 42 are mounted to base 38 via an interference fit. Each septum 48 provides resealable access structure for a needle to access either of internal chambers 50, 52 of port 22. Cap 40 includes a tactile ring 44 which can be felt through the patient's skin by the caregiver seeking to identify the location of septum 48 and cap 40. Cap 42 defines a second tactile ring 46 having a different feel relative to tactile ring 44. The differences in feel between tactile ring 46 and tactile ring 44 provide convenient structure for locating a particular cap 40, 42.

In a preferred embodiment, ring 44 has a higher profile relative to ring 46 (See FIG. 2, for example). The Figures illustrate ring 44 also having a wider profile than ring 46 (See FIG. 7, for example). In the embodiment shown, ring 4 is defined by a generally half torus (donut) shape where a semicircle is rotated in a circular manner about the longitudinal axis of cap 40. Ring 46 is similarly configured, although with a different sized semicircular portion. A configuration of rings 44, 46 that is believed to work satisfactorily to differentiate ring 44 from ring 46 when port 22 is under the skin of a human is to provide semicircular portion 160 of ring 44 with a diameter of 0.174 inches, and to provide semicircular portion 162 with a diameter of 0.060 inches, with both caps having an open central region permitting access to the septums of about 0.450 inches diameter. Both semicircular diameters are rotated about the longitudinal axis of each respective cap 40, 42. The semicircular cross-sectional configuration-of ring 44 is best shown in FIG. 8.

Caps 40, 42 are press fit into housing 38 and axially and radially compress each septum 48. Each septum 48 is a generally cylindrical member prior to being positioned in port 22 with caps 40, 42 being press fit into position. Once operably compressed, a central portion of each septum 48 on each side of each septum 48 is convexly shaped.

It is to be appreciated that port 22 with base 38, and caps 40, 42 can have other shapes and constructions. The embodiment shown includes base 38 and caps 40, 42 made of biocompatible metal. Other materials are possible such as an all plastic or other non-metal construction, or combinations of plastic/other non-metal materials and metal, for example.

Within port 22, two small connecting passages, or angled bores 54, 56 extend outwardly, one from each chamber 50, 52. Each small bore 54, 56 extends in a direction that would intersect one another. Each small bore 54, 56 joins the respective internal chambers 50, 52 to a large central opening, or bore 58. Positioned in large central bore 58 are outlet tubes 34, 36. Each outlet tube 34, 36 includes an outside surface 60, 62 and a proximal end 64, 66 in fluid communication with each chamber 50, 52 and an opposite distal end 68, 70 which extends from port 22. Between ends 64, 66 and ends 68, 70 is a bend region 72, 74. The bend regions 72, 74 permits ends 68, 70 to extend generally parallel in side-by-side fashion away from port 22. As shown in greater detail in FIG. 11, end 68 of outlet tube 34 includes a tapered tip 76 with rounded edges to protect catheter 24 when catheter 24 is mounted to end 68. End 70 is similarly configured. Needle tips are also possible for ends 68, 70.

Insert 78 facilitates mounting of outlet tubes bore 54 and rotated about an axis defined by end 64 to 34, 36 to housing 38. Outlet tube 34 is inserted into make room for outlet tube 36 in bore 56. Alternatively, outlet tube 34 can be inserted into bore 54 in the rotated position initially. Once outlet tube 36 is inserted into bore 56, outlet tube 34 is rotated about the axis defined by end 64, and if necessary, outlet tube 36 is rotated about an axis defined by end 66 of outlet tube 36 such that ends 68, 70 are parallel. Ends 64, 66 extend generally transverse to one another. Once each outlet tube 34, 36 is properly inserted into the positions shown into housing 38, insert 78 is slid along ends 68, 70 toward housing 38 to assemble port 22. A first end 80 of insert 78 fits into central bore 58. A second end 82 protrudes from housing 38 as best shown in FIGS. 3 and 5. First end 80 has a smaller outside diameter than second end 82. The larger diameter of second end 82 meets the smaller diameter of first end 80 at a shoulder 84. Shoulder 84 engages an edge of housing 38 defining the outer periphery of bore 58. Bends 72, 74 of outlet tubes 34, 36 are positioned between first leg 86 and second leg 88 of insert 78. Ends 68, 70 also pass through a first bore 90, and a second bore 92, respectively of insert 78. A slot 94 cut in the shape of an oval (parallel sides and semicircular ends) provides recessed region which permits each bend 72, 74 to be received at least partially within the recess defined by slot 94 for clearance purposes for tubes 34, 36. In the embodiment shown, insert 78 is made from biocompatible metal and is welded to metal base 38. Further, tubes 34, 36 are welded to metal base 38.

Insert 78 further includes a planar end surface 96 surrounded by an angled Surface 98. Planar surface 96 generally lies in a plan perpendicular to a longitudinal axis defined by each end 68, 70 of each outlet tube 34, 36. Angled surface 98 diverges away from outlet tubes 34, 36 in a direction away from port 22 and defines a concave shape. Insert 78 further includes two bayonets or pills 100 on opposite sides of a cylindrical outer surface 85. Only one bayonet 100 is visible in the Figures. The second bayonet is located 180 degrees away on insert 78. As shown in the Figures, angled surface 98 surrounds outlet tubes 34, 36. Preferably, angled surface 98 defines a truncated conical shape and circumscribes a longitudinal axis of insert 78. A curved surface for angled surface 98 is also possible instead of the truncated conical surface shown. Outlet tubes 34, 36 are positioned on opposite sides of the longitudinal axis of insert 78. If portal assembly is a single port construction, then the single outlet tube would be concentric with the longitudinal axis.

A sleeve 102 engages an exterior surface of catheter 24. In particular, sleeve 102 has an inside surface 104 defining an inner diameter smaller than the outer diameter defined by the outside surface of catheter 24 when catheter 24 is engaged elastically with outlet tubes 34, 36. Such configuration permits sleeve 102 to draw, or drag catheter 24 toward angled surface 98 and end surface 96 to form a bunched up wedge-shaped portion 32a with an end 32 of catheter 24 as shown in FIG. 6. An interference it of about three- to four-thousandths of an inch between the inside diameter of sleeve 102 and catheter 24 in the stretched state works adequately. For example, in a portal assembly 20 with the outlet tubes 34, 36 each having about 0.065 inch diameters, and located at centers spaced at about 0.073 inches apart, and the silicone catheter 24 with an outer radius of about 0.067 inches (unstretched), and dual lumens 30, 31 of about 0.044 inches in diameter and spaced apart centers at about 0.060 inches, a sleeve 102 having an inside diameter of about 0.142 inches is useful in drawing the catheter 24 appropriately toward angled surface 98. In the embodiment shown, sleeve 102 is made from biocompatible materials, such as polycarbonate or other plastic.

Sleeve 102 includes an outside surface 106 which includes a first lip 108 and a second lip 110 for retaining sleeve 102 with lock ring 120. Between first lip 108 and second lip 110 is a recessed channel 112. Recessed channel 112 permits sleeve 102 to rotate relative to lock ring 120. Recessed channel 112 is provided with a length that permits sleeve 102 to move longitudinally relative to lock ring 120.

Sleeve 102 includes an end 114 which facilitates the wedging action of catheter 24 during use. End 114 includes an angled surface 116 defining a convex shape for use in providing a space for receipt of additional bunched up catheter if necessary. Preferably, surface 116 is a truncated conical shape.

End 114 of sleeve 102 preferably also includes a curved, or more preferably, a radiussed inner edge 117. Edge 117 is shown in greater detail in FIG. 12. Preferably, such radiussed edge 117 extends the inner diameter of sleeve 102 slightly more, such as on the order of about six-thousandths of an inch in the embodiment shown, than the rest of the inner diameter of sleeve 102. A radius of about 0.008 inches is one example of the shape for edge 117.

Lock ring 120 includes a solid end ring 122. An inwardly projecting lip 124 has opposed end surfaces which engage either of lip 108 or lip 110 of sleeve 102 to retain sleeve 102 with lock ring 120. In the configuration shown, sleeve 102 is both slidable longitudinally relative to lock ring 120, and rotatable relative to lock ring 120. Relative rotation permits lock ring 120 to rotate relative to sleeve 102 during the locking operation so that sleeve 102 remains engaged with catheter 24 and does not twist catheter 24 relative to outlet tubes 34, 36. This is especially advantageous in the dual port configuration. In the embodiment shown, sleeve 102 is snap fit to lock ring 120. The longitudinal relative movement is useful for ease of assembly and ease of use, although such feature is optional.

Lock ring 120 includes two slots 126, 127 which cooperate with bayonets 100 of insert 78 to mount lock ring 120 to insert 78. Slots 126, 127 are generally identically shaped on opposite sides of lock ring 120. Slot 126 is configured as a cam surface 128 which provides camming action of lock ring 120 relative to insert 78, thereby providing a mechanical advantage for the bunching up and the radially inwardly forcing of catheter 24. Cam surface 18 can be angled as desired to vary the force applied to catheter 24 to engage angled surface 98. To assist in hand turning of lock ring 120, outwardly extending wings or lever arms 132 are provided extending from a central portion of lock ring 120. Recess 134 of port 22 is configured to fairly closely receive wings 132 Of lock ring 120 as shown in FIGS. 1 and 6, for example. Such recess 134 is useful to prevent ingrowth region by reducing the spaces between the projecting members of portal assembly 20. Lock ring 120 is shown as being turned in a clockwise direction to tighten catheter 24 against outlet tubes 34, 36 and insert 78. A counterclockwise arrangement is also possible (not shown).

Slot 126 includes an overcenter surface or detent 130 which locates bayonet 100 to hold lock ring 120 in the locked position, as best shown in FIGS. 1, 4, and 7. An axial force is exerted on lock ring 120 by catheter 24 in a direction away from insert 78. In the position shown, bayonet 100 cannot work its way past detent 130 and along cam surface 128 to possibly inadvertently allow catheter 24 to become separated from port 22. Also, detent 130 Will not allow an errant needle to unlock lock ring 20. Further, the surgeon will realize instantly that connector 26 is properly locked when bayonet reaches detent 130 during connection of catheter 24 to port 22. A similar detent is provided for the other bayonet 100.

Instead of the bayonet/slot arrangement for locking ring 120 to insert 78, other lock structures are possible such as Luer threads or tapered pipe threads.

Connector 26 generally includes the two outlet tubes 34, 36, the angled surface 98, the sleeve 102, and the lock ring 120 with slots 126, 127 and the bayonets 100 of insert 78. Together, outlet tubes 34, 36 and angled surface 98, and in some cases surface 96, form a base arrangement portion of the connector 26. Sleeve 102 and lock ring 120 form a sleeve arrangement portion of connector 26. Lock ring 120 with slots 126, 127 and bayonets 100 of insert 78 form holding structure for holding the sleeve relative to the base arrangement portion to permit connection to catheter 24. Sleeve 102 and lock ring 120 can be constructed as an integral unit if desired, where no relative rotation or longitudinal sliding movement is possible. Connector 26 is useable not only in portal assembly 20, but other structures where it is desired to securably connect a device and a catheter.

A preferred use of connector 26 with catheter 24 and port 22 positions by hand the end 32 of catheter 24 over the ends 68, 70 of outlet tubes 34, 36 as shown in FIG. 5 and in dashed lines in FIG. 3. It is preferred that catheter 24 not be pushed by hand past the general position shown, unless provision is made for the additional bunched up catheter 24 that would result if catheter 24 were initially pushed by hand past the position shown in FIG. 3. If catheter 24 is pushed too far, it may be difficult to form the appropriate bunched up end 32a of the catheter 24, unless provision is made for the excess material. In the embodiment shown, about 1 to 4 millimeters of catheter 24 positioned on outlet tubes 34, 36 is adequate. The convex shape of end 114 of sleeve 102 allows for some variation in the amount of bunched up catheter 24 in connector 26. Catheter 24 can be pushed by hand all the way until the end 30 engages surface 96. In that case, if not already present, room must be provided to accommodate the additional bunched up catheter 24 once sleeve 102 is drawn by lock ring 120 toward insert 78.

Before or after positioning catheter 24 on outlet tubes 34, 36, catheter 24 is threaded through lock ring 120 and sleeve 102. In a typical implantation surgery, the distal end of catheter 24 is threaded into the body to the desired location, the proximate end 32 of catheter 24 is threaded through sleeve 102 and lock ring 120, then the proximate end 32 of catheter 24 is positioned on outlet tubes 34, 36. Next, lock ring 120 and sleeve 102 are moved toward port 22 in the direction of arrow A as shown in FIG. 3 until bayonets 100 are lined up adjacent the respective slots 126, 127. Next, lock ring 120 is rotated the direction of arrow B with each bayonet 100 moving along within slot 126, 127 toward detent 130. For the counterclockwise arrangement, lock ring 120 would be turned in a direction opposite to arrow B to tighten.

Rotation of lock ring 120 further draws sleeve 102 toward angled surface 98 of port 22. This bunches up end 32 of catheter 24 to create the thickened wedge shape 32a as shown in FIG. 6 when the end 32 of catheter 24 engages angled surface 98. Catheter 24 will also bunch up due to engagement with planar surface 96. Lock ring 120 is in the locked position once bayonet 100 is positioned in detent 130 as shown in FIGS. 4 and 6. Catheter 24 is in this position bunched up within an interior of the connector 26, as shown in FIG. 7 to have a wall portion thicker than the catheter wall portion in either the unstretched state or the stretched state (on tubes 34, 36). In particular, catheter 24 includes a bunched up, wedge-shaped end 32a which is wedged against angled surface 98. This wedging action provides a normal force on catheter 24 to seal against outlet tubes 34, 36. The combination of the axial force and the circumferential force on catheter 24 provides an advantageous connection. Such wedge action helps eliminate cross talk between first lumen 30 and second lumen 31. Cross talk can occur in the region between lumens 30, 31 due to the stretching of first and second lumens 30, 31 that occur when catheter 24 is positioned on ends 68, 70 of outlet tubes 34, 36. The normal force helps to seal catheter 24 and reduce cross talk. The bunched up end 32a of catheter 24 also cannot be pulled out easily from connector 26 since it is captured by end 114 of sleeve 102.

Once connector 26 is placed in the position shown in FIGS. 1, 2, 4, and 6, catheter 24 is sealed to port 22 such that fluid from chambers 50, 52 will pass in a fluid tight passage through outlet tubes 34, 36 and through catheter 24 for delivery to the infusion site. Similarly, any fluids withdrawn from port 22 will be drawn from the distal end of catheter 24. The sleeve 102 helps seal catheter 24 to outlet tubes 34, 36 due to the interference fit of edge 117. Also, the stretched catheter 24 will to some degree seal itself on tubes 34, 36 due to the outlet tubes 34, 36 being sized larger than lumens 30, 31.

The bunched up, wedge-shaped portion 32a at least partially contributes to forming the seal between catheter 24 and outlet tubes 34, 36. In addition, the bunched up, wedge-shaped portion 32a is trapped and performs an anchor function to resist pull out forces applied to catheter 24 acting to separate catheter 24 from outlet tubes 34, 36. The angled surface 98 and the angled end 114 selectively contains the outward expansion of bunched up end 32a caused by sleeve 102 and utilizes such containment to provide an advantageous seal and/or an advantageous anchor of catheter 24 to port 22 from being pulled out.

The axial force exerted by catheter 24 on lock ring 120 to maintain bayonets in detents 130 can be overcome by an appropriate rotational force applied to lock ring 12 in a direction opposite to the arrow B shown in FIG. 3.

An end 109 of sleeve 102, especially when sleeve 102 is made from resilient materials such as plastic, functions to relieve bending strains applied to catheter 24 to resist pull out of catheter 24 or breakage or other damage from engagement of catheter 24 and connector 26. Sleeve 102 also functions as a catheter protector from errant needles that could otherwise puncture or cut catheter 24. The strain relief function and the catheter protector function for sleeve 102 are optional.

To remove catheter%24, lock ring 120 is turned in a direction opposite to arrow B to release catheter 24 to permit pull off from outlet tubes 34, 36.

Housing 38 also includes a plurality of suture holes 136. Formed adjacent suture holes 136 are depressions 138 which extend inwardly from an outer surface portion 146 of housing 38. With depressions 138, a shorter suture hole 36 results. Each suture hole 136 includes a guide surface or lead-in 140 adjacent a bottom surface 162. Each lead-in 140 is sized larger than the cylindrical passage defined by suture hole 136. Each lead-in tapers to the cylindrical passage of suture hole 136. Lead-ins 140 make it easier for the surgeon to thread the needle through each suture hole 136 during surgery from the bottom toward the top of portal assembly 20.

Depressions 144 on selected areas of bottom surface 142 reduce the weight of housing 38 and yet provide a stable base for portal assembly 20 to be mounted to a portion of the body.

Each internal chamber 50, 52 includes a curved inside bottom surface 51 at the bottom of each chamber. These curved surfaces 51 reduce dead spots in the portal assembly 20 to prevent stagnation of fluids and other materials from collecting over time. Preferably bottom surfaces 51 each define a complex curve, preferably a large radiussed central region 150, and a small radiussed peripheral region 152. In one preferred embodiment, central region 50 is curved at a radius of 0.74 inches and peripheral region 152 is curved at a radius of 0.05 inches, for example.

It must be understood, however, that even though numerous advantages and characteristics of the invention have been set forth in the foregoing description, together with details of the structure and function of the invention, the disclosure is illustrative only, and changes may be made in detail, especially in matters of shape, size and material components within the principals of the invention, to the full extent indicated by the broad, general meanings of the terms in which the appended claims are expressed.

What is claimed is:

1. A portal assembly for connecting to a catheter comprising:
   a port with a first resealable septum;
   a first tube extending from the port, the first tube sized to be received inside the catheter;
   wherein the port defines a plurality of suture holes, each suture hole having a first cylindrical passage, each suture hole having a lead-in sized larger than the first cylindrical passage and tapering to the first cylindrical passage; and
   wherein the port further defines a plurality of depressions, each depression positioned adjacent one of the suture holes at an end opposite to an end defining the lead-in of each suture hole.

2. The portal assembly of claim 1, further comprising a connector for mounting the catheter to the first tube.

3. The portal assembly of claim 2, further comprising a catheter, the connector mounting the catheter to the first tube.

4. A portal assembly for connecting to a catheter comprising:
   a port with a first resealable septum;
   a first tube extending from the port, the first tube sized to be received inside the catheter; and
   wherein the port defines an internal chamber, the septum permitting access to the internal chamber, the first tube in fluid communication with the internal chamber, the internal chamber including a bottom surface facing opposite the septum wherein the bottom surface is defined by a complex curve including a first large radius defining a central portion and second smaller radius defining a periphery around the central portion.

5. The portal assembly of claim 4, further comprising a connector for mounting the catheter to the first tube.

6. The portal assembly of claim 5, further comprising a catheter, the connector mounting the catheter to the first tube.

7. A portal assembly comprising:

a port with a first resealable septum and a second resealable septum, wherein the port includes first and second rings, the first ring surrounding the first septum, the second ring surrounding the second septum, the first ring having a first continuous portion having a cross-section defined by a first height projecting upward around the first septum, the second ring having a second continuous portion having a cross-section defined by a second height projecting upward around the second septum, the first height differently sized from the second height;

a first tube extending from the port; and a second tube extending from the port.

8. The portal assembly of claim 7, wherein the first and second tubes are side by side, and further comprising a connector for mounting a catheter to the first and second tubes, the connector sized to surround both of the first and second tubes.

9. The portal assembly of claim 8, further comprising a catheter, the connector mounting the catheter to the first and second tubes.

10. The portal assembly of claim 7, wherein the cross-section of the first ring has a first width perpendicular to the first height, and the cross-section of the second ring has a second width perpendicular to the second height, the first width differently sized from the second width.

11. The portal assembly of claim 10, wherein the first height is larger than the second height, and the first width is larger than the second width.

\* \* \* \* \*